US012697405B2

(12) United States Patent
Miranda Razo et al.

(10) Patent No.: US 12,697,405 B2
(45) Date of Patent: Aug. 4, 2026

(54) METHOD AND SYSTEM FOR TEXTILES DISINFECTION IN HOUSEHOLD APPLIANCE

(71) Applicant: CONTROLADORA MABE, S.A. DE C.V., Mexico City (MX)

(72) Inventors: Victor Hugo Miranda Razo, Querétaro (MX); Guillermo Astorga Peralta, Querétaro (MX)

(73) Assignee: CONTROLADORA, MABE S.A. DE C.V., Mexico City (MX)

( * ) Notice: Subject to any disclaimer, the term of this patent is extended or adjusted under 35 U.S.C. 154(b) by 749 days.

(21) Appl. No.: 17/947,775

(22) Filed: Sep. 19, 2022

(65) Prior Publication Data

US 2023/0190971 A1     Jun. 22, 2023

(30) Foreign Application Priority Data

Dec. 17, 2021     (MX) .................... MX/a/2021/016020

(51) Int. Cl.
| | |
|---|---|
| *A61L 2/10* | (2026.01) |
| *A61L 2/26* | (2006.01) |
| *A61L 103/50* | (2026.01) |
| *F26B 3/14* | (2006.01) |
| *F26B 23/10* | (2006.01) |

(52) U.S. Cl.
CPC .................................... *A61L 2/10* (2013.01); *A61L 2/26* (2013.01); *F26B 3/14* (2013.01); *A61L 2103/50* (2026.01); *A61L 2202/11* (2013.01); *A61L 2202/122* (2013.01); *F26B 23/10* (2013.01)

(58) Field of Classification Search
None
See application file for complete search history.

(56) References Cited

U.S. PATENT DOCUMENTS

| | | | | |
|---|---|---|---|---|
| 5,664,340 | A | * | 9/1997 | Brown ....................... A61L 2/10 34/275 |
| 6,877,248 | B1 | * | 4/2005 | Cross .................... D06F 58/203 34/275 |
| 8,303,718 | B2 | * | 11/2012 | Kim ....................... D06F 37/267 134/1 |
| 10,814,025 | B2 | | 10/2020 | Bonutti et al. |

(Continued)

FOREIGN PATENT DOCUMENTS

| | | |
|---|---|---|
| AU | 2014393062 | 11/2015 |
| CN | 106012406 | 10/2016 |

(Continued)

*Primary Examiner* — David J Laux
(74) *Attorney, Agent, or Firm* — Terry M. Sanks, Esq.; Beusse Sanks, PLLC

(57)     ABSTRACT

The present invention relates to a UVC technology-based system for disinfecting textiles comprising an ultraviolet light source comprising a power supply; a housing to contain the light source and to protect it from any impact; a control board responsible for controlling the switching on or off of the ultraviolet light source; a driving means that activates the movement of the drum and an electrical resistance that allows the generation of heat to start the drying cycle inside the household appliance. The system allows disinfecting textiles by up to 99.9%, saving energy and, at the same time, reducing the process time and damage to the textiles.

14 Claims, 2 Drawing Sheets

(56)                    References Cited

U.S. PATENT DOCUMENTS

| 2005/0194026 A1 * | 9/2005 | Lu ............................. A61L 2/04 |
| | | 134/105 |
| 2009/0064422 A1 * | 3/2009 | Kim ..................... D06F 37/266 |
| | | 8/137 |
| 2012/0047763 A1 * | 3/2012 | Abramovich ............. F26B 3/28 |
| | | 34/275 |
| 2014/0059881 A1 * | 3/2014 | Kim ..................... D06F 29/005 |
| | | 34/493 |
| 2017/0260681 A1 * | 9/2017 | Gao ........................ D06F 58/10 |
| 2020/0208325 A1 * | 7/2020 | Park ........................ D06F 37/26 |
| 2020/0230267 A1 * | 7/2020 | Greenfield ............. B01J 19/124 |
| 2020/0384140 A1 * | 12/2020 | Hoehne ................... D06F 58/44 |

FOREIGN PATENT DOCUMENTS

| JP | 3229571 | 11/2020 |
| KR | 20070053051 | 5/2007 |
| KR | 100730936 | 6/2007 |
| KR | 101565953 | 11/2015 |
| KR | 101751777 | 6/2017 |

* cited by examiner

METHOD AND SYSTEM FOR TEXTILES DISINFECTION IN HOUSEHOLD APPLIANCE

OBJECT OF THE INVENTION

The present invention refers to a UVC technology-assisted system for disinfecting textiles in a household appliance that allows up to 99.9% disinfection of textiles, saving energy and, at the same time, reducing the process time and damage to textiles.

BACKGROUND

The use of UVC technology for textile disinfection is known in the state of the art, such as AU 2014393062, which refers to a laundry washing machine comprising an external washing tub, a rotating washing drum adapted to receive laundry, and a recirculation circuit comprising a UV source within said recirculation circuit. Said recirculation duct comprises a duct for said liquid to flow through and a seat for receiving said UV source, including a UV-transparent wall, wherein a portion of the UV-transparent wall separates said seat from the duct.

Document KR 100730936 is also known, which describes a drum washing machine that has a sterilizing and deodorizing function capable of disinfecting any microorganisms and bacteria that remain in the laundry during the laundry drying operation and eliminating the odors generated in the drum by residual contaminants. The washing machine is composed of a cabinet, a water storage tank installed horizontally from the top of the base, a drum rotatably installed on the water storage tank, a door, as well as two ultraviolet generating units installed on the washing machine door to radiate ultraviolet rays into the drum.

Another known document is KR 101565953, which refers to an apparatus for the disinfection of laundry using UV LEDs, the invention comprising: a cabin for housing the laundry inside and installed with a door on one surface; a respective UV LED lamp capable of radiating UV light having a wavelength with a disinfection function and a hanger unit configured to work in conjunction with the lamp: when laundry is hung on the hanger unit, the push button is pressed and a hanger signal is transmitted to the control unit so that the UV LED lamp turns on, and when the laundry is removed from the hanger unit, the push button is controlled to return to its original position, transmitting a signal to the control unit controlling the UV LED lamp to turn off.

Document U.S. Pat. No. 5,664,340 protects a dryer designed to remove fungus-causing bacteria and germs in laundry. The present invention consists of ultraviolet mechanisms located inside the door of typical gas and electric dryers, thus eliminating germs from washed laundry. The UV lights are contained within a plate mounted on the dryer door and covered with transparent glass or polycarbonate plastic. When the dryer is on, the ultraviolet lights will shine, thus starting the process of germ removal from the laundry.

Document CN 106012406 describes a washing machine with ultraviolet radiation for a sterilization and disinfection function that includes a washing machine body, an inner tub placed in the washing machine body, the bottom of the inner wall of the inner tub is additionally provided with an impeller, a coil is provided in the impeller, the coil is electrically connected to an ultraviolet lamp which is fixedly installed in the impeller, and a magnetic field generator to act on the connecting coils and generate electric current is provided in the inner tub. When the coils generate current, power is supplied to the lamp, which generates ultraviolet rays and irradiates the laundry to be washed inside the inner tub.

Despite these prior efforts, there is still a need for effective alternatives to existing systems for disinfecting textiles that allow their use in different embodiments and provide additional benefits such as energy savings, shorter process times and less damage to textiles by avoiding using high temperatures for disinfection.

BRIEF DESCRIPTION OF THE INVENTION

The present invention relates to a UVC technology-based system for disinfecting textiles comprising an ultraviolet light source comprising a power supply; a housing to contain the light source and protect it from any impact; a control board responsible for controlling the switching on or off of the ultraviolet light source, depending on the embodiment in which the invention is used; a driving means that activates the movement of the drum and an electrical resistance that allows the generation of heat to start the drying cycle inside the household appliance.

The ultraviolet light generated by the light source is within the wavelength range of 250 to 290 nm (short wave or UVC) to eliminate up to 99.9% of viruses and bacteria, reducing the number of microorganisms present on the textiles and preventing their growth inside the household appliance, thus preventing them from being transferred to the textiles to be placed inside in the next cycle.

BRIEF DESCRIPTION OF THE DRAWINGS

The illustrative embodiment can be described with reference to the accompanying figures, whereby.

DETAILED DESCRIPTION OF THE INVENTION

Figure 1:
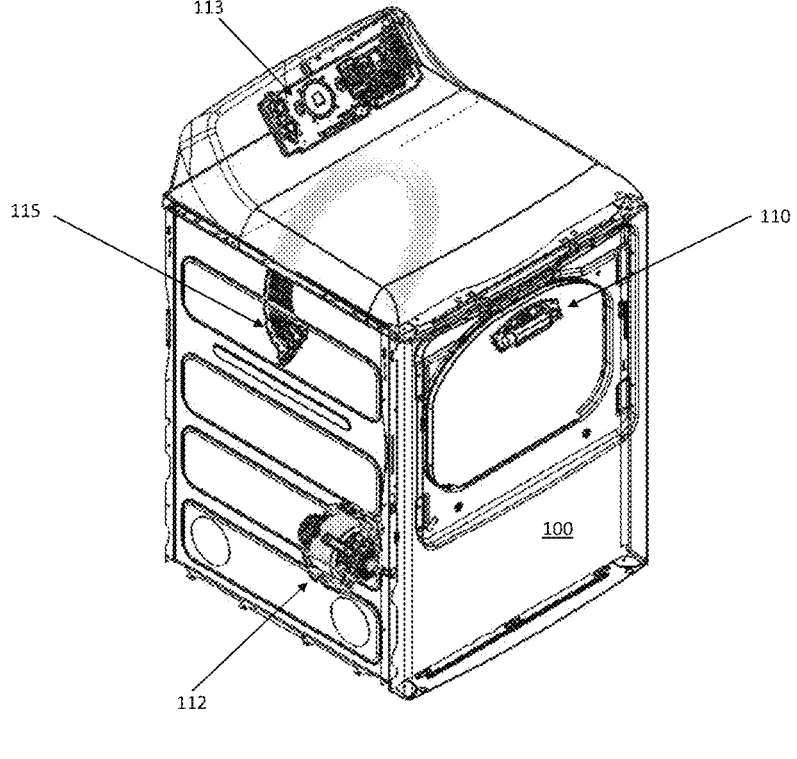
FIG. 1 illustrates a front right perspective view of the UVC technology-based system for disinfecting textiles applied in a dryer.

The following detailed description is exemplary only and is not intended to limit the described embodiments or the application and uses of the described embodiments. As used herein, the word "exemplary" or "illustrative" means "serving as an example, instance, or illustration." Any implementation described herein as "exemplary" or "illustrative" should not necessarily be construed as preferred or advantageous over other implementations. All of the implementations described below are exemplary implementations provided to enable those skilled in the art to make or use the embodiments of the disclosure and are not intended to limit the scope of the disclosure. For the purposes of the present description, the terms "upper", "lower", "left", "posterior", "right", "front", "vertical", "horizontal" and their derivatives will refer to the invention as oriented in the figures. In addition, there is no intention to be subject to any explicit or implicit theory presented in the technical field above, background, brief summary or the following detailed description.

It should also be understood that the specific devices and processes illustrated in the accompanying drawings, and described in the following specification, are simply exemplary embodiments of the inventive concepts defined in the attached claims. Therefore, the specific dimensions and other physical characteristics related to the embodiments described herein should not be considered as limiting, unless the claims expressly state otherwise.

The present invention may present several modifications and alternative constructions, some of which are detailed in the drawings below. However, it should be clear that the intention is not to limit the invention to a particular embodiment or form, but rather the present invention should cover changes, additions and modifications as part of its scope. Independent aspects and advantages of the present invention will become apparent to those skilled in the art upon review of the detailed description and drawings.

Figure 2:
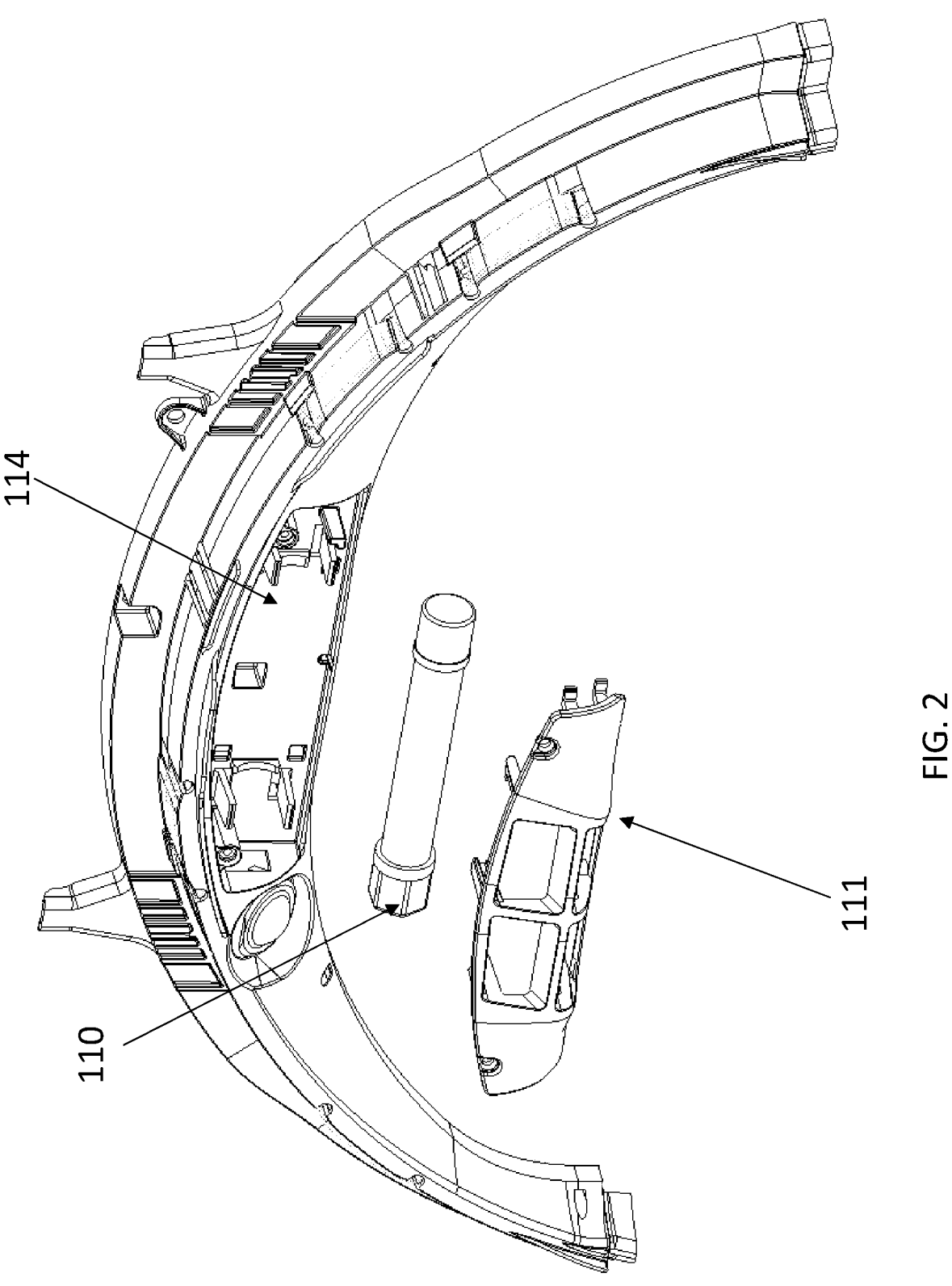
FIG. 2 illustrates a detailed view of the light source assembly in a dryer.

The present invention relates to a system for disinfecting textiles in a household appliance (100) comprising an ultraviolet light source (110) that is activated by a power supply. In a preferred embodiment, the power supply (110) comprises electronic means. Preferably, the power supply (110) is an electrical ballast. Said ultraviolet light source (110) is configured to be installed inside the drum of the household appliance. In the illustrated embodiment, said ultraviolet light source (110) is installed in an inner region of the drum that can directly irradiate the textiles, preferably in the upper bearing of a dryer drum (FIG. 2).

In one embodiment of the invention, the ultraviolet light source (110) is selected from the group comprising at least one lamp, at least one array of LEDs, or combinations thereof. The lamp can be any selected by the person skilled in the art, for example, a halogen lamp or a bulb lamp.

Said ultraviolet light source (110) has the function of radiating ultraviolet light onto the textiles inside the drum and to the internal components of the household appliance, for example, the drum, baffles, air diffuser and suction duct to eliminate up to 99.9% of viruses and bacteria, reducing the amount of microorganisms present in the textiles and preventing their growth inside the household appliance, thus preventing them from being transferred to the textiles to be placed inside in the next cycle.

In one embodiment of the invention, the ultraviolet light source (110) is placed inside a housing (114) comprising a grid (111) to protect it from any impact, which can be made of any suitable material, for example, plastic or quartz.

In a preferred embodiment of the invention, the ultraviolet light is short-wave (UVC) to enable efficient removal of microorganisms from the textiles. Therefore, its wavelength ranges from about 250 nm to about 290 nm.

The invention also comprises a control board (113) responsible for controlling switching the ultraviolet light source (110) on or off, depending on the embodiment in which the present invention is used, as will be detailed later. Said control board (113) is also responsible for turning on or off a driving means (112) that activates the movement of the drum and a heat source (115) that allows the generation of heat to start the drying cycle inside the household appliance. The heat source (115) may comprise an electrical resistance or a combustion system.

The system of the present invention is intended to be applied in a dryer, preferably an open cycle dryer, as well as in a dryer with a heat pump or with a condensing system.

The present invention also provides a UVC technology-based method for disinfecting textiles, said method being able to have different embodiments, as detailed below.

In a first embodiment, the UVC light disinfection system of the present invention can be applied in any drying cycle, activating or deactivating the ultraviolet light source (110) by means of the control board (113), at the convenience of the user. In this embodiment, the ultraviolet light source (110) is on 100% of the time.

In a second embodiment, the system is applied in a special disinfection cycle comprising stopping the movement of the drum and turning the ultraviolet light source (110) on at controlled time intervals; that is, prior to the end of a drying cycle, the control board (113) deactivates the driving means (112) of the drum, stopping its movement so that the ultraviolet light source (110) irradiates all the components of the household appliance and the textiles inside it. This pattern (stopping the movement of the drum and irradiating all the components of the household appliance together with the textiles with ultraviolet light) can be repeated as many times as necessary.

As an example, a possible disinfection cycle for a drying process with a total duration of 1.5 hours is described below.

Pause #1: 1-minute pause (deactivation of the driving means) and radiation of UVC light Drum rotation for 13 seconds Pause #2: 1-minute pause (deactivation of the driving means) and radiation of UVC light Drum rotation for 13 seconds Pause #3: 1-minute pause (deactivation of the driving means) and radiation of UVC light Drum rotation for 13 seconds As the person skilled in the art must understand, the number of pauses and rotations are parametric, so they can be adjusted according to the needs of each case.

In a third embodiment, UVC light and heat are applied alternately. The duration and number of applications between one technology and another will be defined by the person skilled in the art, according to the specific needs of each case.

The method and system of the present invention allow to efficiently reduce the amount of microorganisms in the textiles, as well as to reduce the time of the drying cycle (up to 50%), since disinfection is carried out within the same drying cycle, which also allows for energy savings and less damage to the textiles by reducing the process time and the use of high temperatures. In addition, the proposed method provides a flexible alternative to existing methods, since it allows its application in different embodiments, at the user's convenience.

A person skilled in the art can modify the structure described herein. However, it should be noted that this description relates to preferred embodiments of the invention, and is provided for illustrative purposes only, and should not be understood as limiting the invention. All obvious modifications in the spirit of the invention, such as changes in the shape, material, and dimensions of the elements that make up the invention, should be considered within the scope of the attached claims.

The invention claimed is:

1. A method for disinfecting textiles to eliminate up to 99.9% of viruses and bacteria in a household appliance with a drum and an ultraviolet light source located on the upper bearing of a dryer drum, comprising:

stopping the movement of the drum and turning on the ultraviolet light source for a certain time to irradiate the textiles and internal components of said household appliance prior to the end of a drying cycle; and repeating stopping the movement of the drum and turning the ultraviolet light source for a certain period of time;

wherein controlling a movement of the drum and switching on the light source is carried out by means of an electronic card a control board in communication with said elements the drum and the light source.

2. The method for disinfecting textiles to eliminate up to 99.9% of viruses and bacteria in a household appliance with a drum of claim 1, wherein the wavelength of the ultraviolet light radiated by the ultraviolet light source is in the range of about 240 nm to about 290 nm.

3. The method for disinfecting textiles to eliminate up to 99.9% of viruses and bacteria in a household appliance with a drum of claim 1, wherein the ultraviolet light source is turned on while the drum is in motion.

4. The method for disinfecting textiles to eliminate up to 99.9% of viruses and bacteria in a household appliance with a drum of claim 1, wherein the time the drum stops is about 1 minute and wherein the time during which the ultraviolet light source is turned on is about 13 seconds.

5. The method for disinfecting textiles to eliminate up to 99.9% of viruses and bacteria in a household appliance with a drum of claim 1, wherein high levels of disinfection for the textiles and the internal components heat by means of a heat source the household appliance are achieved avoiding potential cross-contamination between different drying cycles.

6. A system for disinfecting textiles to eliminate up to 99.9% of viruses and bacteria in a household appliance with a drum that allows to efficiently reduce the amount of microorganisms in the textiles and the time of the drying cycle resulting in energy savings and less damage to the textiles, comprising:

an ultraviolet light source located on the upper bearing of a dryer drum to avoid the use of a reflector, that radiates ultraviolet light onto the textiles inside the drum and to the internal components of the household appliance;
    a power supply to activate the ultraviolet light source;
    a housing for housing the ultraviolet light source, wherein the housing is inside the drum of the household appliance and comprises a grid to protect the ultraviolet light source from any impact;
a driving means that activates the movement of the drum; and
    a control board in communication with the power supply of the ultraviolet light source and the driving means to control their activation/deactivation,
    wherein the control board stops the movement of the drum and turns the ultraviolet light source for a certain time to irradiate the textiles and internal components of said household appliance prior to the end of a drying cycle, wherein the control board repeats the stop of the movement of the drum and turns the ultraviolet light source for a certain time.

7. The system for disinfecting textiles to eliminate up to 99.9% of viruses and bacteria in a household appliance with a drum of claim 6 that allows up to 99.9% disinfection of both textiles and to internal components of the household appliance.

8. The system for disinfecting textiles to eliminate up to 99.9% of viruses and bacteria in a household appliance with a drum of claim 6, further comprising a heat source to generate heat inside the household appliance, wherein said heat source is also controlled by the control board.

9. The system for disinfecting textiles to eliminate up to 99.9% of viruses and bacteria in a household appliance with a drum of claim 8, wherein the heat source comprises an electrical resistance or a combustion system.

10. The system for disinfecting textiles to eliminate up to 99.9% of viruses and bacteria in a household appliance with a drum of claim 6, wherein the ultraviolet light source is selected from the group comprising at least one lamp, at least one array of LEDs or combinations thereof and wherein the ultraviolet light radiated by said ultraviolet light source has a wavelength ranging from about 250 nm to about 290 nm.

11. The system for disinfecting textiles to eliminate up to 99.9% of viruses and bacteria in a household appliance with a drum of claim 10, wherein the lamp is selected from a halogen lamp or a bulb lamp.

12. The system for disinfecting textiles to eliminate up to 99.9% of viruses and bacteria in a household appliance with a drum of claim 6, wherein the power supply comprises an electronic means.

13. The system for disinfecting textiles to eliminate up to 99.9% of viruses and bacteria in a household appliance with a drum of claim 12, wherein the power supply is an electrical ballast.

14. The system for disinfecting textiles to eliminate up to 99.9% of viruses and bacteria in a household appliance with a drum of claim 6, wherein the household appliance is a dryer.

* * * * *